US008679819B2

(12) United States Patent
Kawaoka

(10) Patent No.: US 8,679,819 B2
(45) Date of Patent: Mar. 25, 2014

(54) MUTANT CELLS WITH ALTERED SIALIC ACID

(75) Inventor: Yoshihiro Kawaoka, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 276 days.

(21) Appl. No.: 11/644,179

(22) Filed: Dec. 22, 2006

(65) Prior Publication Data

US 2008/0009031 A1 Jan. 10, 2008

Related U.S. Application Data

(62) Division of application No. 10/081,170, filed on Feb. 22, 2002, now Pat. No. 7,176,021.

(60) Provisional application No. 60/271,044, filed on Feb. 23, 2001.

(51) Int. Cl.
*C12N 7/00* (2006.01)
*C12N 5/00* (2006.01)

(52) U.S. Cl.
USPC ...................................... 435/235.1; 435/325

(58) Field of Classification Search
None
See application file for complete search history.

(56) References Cited

U.S. PATENT DOCUMENTS

| 6,843,996 B1 | 1/2005 | Parkin et al. |
| 7,176,021 B2 | 2/2007 | Kawaoka |
| 2004/0002061 A1 | 1/2004 | Kawaoka |
| 2004/0132164 A1 | 7/2004 | Doyle et al. |
| 2007/0231348 A1 | 10/2007 | Kawaoka et al. |
| 2009/0324640 A1 | 12/2009 | Kawaoka et al. |

FOREIGN PATENT DOCUMENTS

| JP | 07-203958 | | 8/1995 |
| WO | WO-03068923 | A2 | 8/2003 |
| WO | WO-2006051069 | A2 | 5/2006 |
| WO | WO-2008147496 | A2 | 12/2008 |
| WO | WO-2008147496 | A3 | 12/2008 |

OTHER PUBLICATIONS

Green et al. J. Cell Biol. 89: 230-239, 1981.*
Brandli, A. W., et al., "A Polarized Epithelial Cell Mutant Deficient in Translocation of UDP-galactose into the Golgi Complex", *Journal of Biological Chemistry*, 263(31), (Nov. 5, 1988),16283-16290.
Hughes, Mark T., "Adaptation of Influenza A Viruses to Cells Expressing Low Levels of Sialic Acid Leads to Loss of Neuraminidase Activity", *Journal of Virology*, 75 (8), (Apr. 2001),3766-3770.
Hughes, Mark T., "Influenza A Viruses Lacking Sialidase Activity Can Undergo Multiple Cycles of Replication in Cell Culture, Eggs, or Mice", *Journal of Virology*, 74 (11), (Jun. 2000),5206-5212.
Ito, T , et al., "Differences in Sialic Acid-Galactose Linkages in the Chicken Egg Amnion and Allantois Influence Human Influenza Virus Receptor Specificity and Variant Selection", *Journal of Virology*, 71 (4), (Apr. 1997),3357-3362.
Liu, Chongguang , "Influenza type A virus neuraminidase does not play a role in viral entry, replication, assembly, or budding.", *Journal of Virology*, 69(2), (Feb. 1995),1099-106.
Liu, Chongguang , "Selection and characterization of a neuraminidase-minus mutant of influenza virus and its rescue by cloned neuraminidase genes.", *Virology*, 194(1), (1993),403-407.
Martin, J. , et al., "Studies of the Binding Properties of Influenza Hemagglutinin Receptor-Site Mutants", *Virology*,241(1 )., Feb. 1, 1998 ,101-111.
Masuda, H. , et al., "Substitution of Amino Acid Residue in Influenza A Virus Hemagglutinin Affects Recognition of Sialyl-Oligosaccharides Containing N-Glycolylneuraminic Acid", *FEBS Letters*, 464, (1999),71-74.
Matta, M , et al., "Cell-Surface Sialoglycoconjugate Structures in Wild-Type and Mutant Crithidia Fasciculata", *Parasitol Res*, 85, (1999),293-299.
Neumann, Gabriele , et al., "Generation of Influenza A Viruses Entirely from Cloned cDNAs", *Proceedings of the National Academy of Sciences USA*, 96, (Aug. 1999),9345-9350.
Ray, Manas K., et al., "A novel glycosylation phenotype expressed by Lec23, a Chinese hamster ovary mutant deficient in alpha-glucosidase I", *Journal of Biological Chemistry*, 266(34), (Dec. 5, 1991),22818-22825.
Schultz-Cherry, S. , et al., "Influenza Virus NS1 Protein Induces Apoptosis in Cultured Cells", *Journal of Virology*, 75, (Sep. 2001),7875-7881.
Takeda, T. , et al., "Expression of Podocalyxin Inhibits Cell-Cell Adhesion and Modifies Junctional Properties in Madin-Darby Canine Kidney Cells", *Molecular Biology of the Cell*, 11, (Sep. 2000), 3219-3232.
Yang, Ping , "Hemagglutinin specificity and neuraminidase coding capacity of neuraminidase-deficient influenza viruses.", *Virology*, 229(1), (1997),155-165.
"U.S. Appl. No. 12/113,690, Restriction Requirement mailed Apr. 6, 2010", 10 pgs.
"European Application Serial No. 02724994.5, Office Action mailed Mar. 27, 2009", 2 pgs.
"International Application No. PCT/US2008/005641, Search Report mailed Feb. 4, 2009", 6 pgs.
"International Application Serial No. PCT/US2008/005641, Written Opinion mailed Feb. 4, 2009", 8 pgs.

(Continued)

*Primary Examiner* — S. Devi
(74) *Attorney, Agent, or Firm* — Schwegman, Lundberg & Woessner, P.A.

(57) ABSTRACT

The invention provides cells useful to propagate influenza virus mutants having reduced sialidase activity.

15 Claims, 2 Drawing Sheets

(56) References Cited

OTHER PUBLICATIONS

Hughes, M. T, et al., "Influenza A viruses lacking sialidase activity can undergo multiple cycles of replication in cell culture, eggs, or mice.", J Virol., 74(11), (Jun. 2000), 5206-212.

Jin, H., et al., "Imparting temperature sensitivity and attenuation in ferrets to A/Puerto Rico/8/34 influenza virus by transferring the genetic signature for temperature sensitivity from cold-adaptive A/Ann Arbor/ 6/60", Journal of virology vol. 78(2), (Jan. 2004), 995-998.

Li, S, et al., "Recombinant influenza A virus vaccines for the pathogenic human A/Hong/Kong/97 (H5N1) Viruses", Journal of Infectious Diseases, Chicago, IL vol. 179(5), (May 1, 1999), 1132-1138.

Liu, Chongguang, "Selection and characterization of a neuraminidase-minus mutant of influenza virus and its rescue by cloned neuraminidase genes.", Virology, 194(1), (1993), 403-407.

Mishin, V. P, et al., "Protection afforded by intranasal immunization with the neuraminidase-lacking mutant of influenza A virus in ferret model", Vaccine, Butterworth scientific. Guildford, GB vol. 23(22), (Apr. 22, 2005), 2922-2927.

Murphy, B. R, et al., "An Influenza A live attenuated reassortant virus possessing three temperature-sensitive mutations in the PB2 Polymerase gene rapidly loses temperature sensitivity following replication in hamsters", Vaccine, Butterworth scientific vol. 15 (12-13), (Aug. 1, 1997), 1372-1378.

Shinya, K., et al., "Characterization of a neuraminidase-deficient influenza a virus as a potential gene delivery vector and a live vaccine", Journal of Virology, 78(6), (Mar. 2004), 3083-3088.

Stray, Stephen J., et al., "Influenza Virus Infection of Desialylated Cells", Glycobiology, vol. 10, No. 7, (2000), 649-658.

"U.S. Appl. No. 10/081,170, Advisory Action mailed Sep. 27, 2004", 3 pgs.

"U.S. Appl. No. 10/081,170, Final Office Action mailed Apr. 12, 2006", 7 pgs.

"U.S. Appl. No. 10/081,170, Final Office Action mailed Jul. 13, 2004", 8 pgs.

"U.S. Appl. No. 10/081,170, Non Final Office Action mailed Jan. 15, 2004", 9 pgs.

"U.S. Appl. No. 10/081,170, Non Final Office Action mailed Feb. 8, 2005", 9 pgs.

"U.S. Appl. No. 10/081,170, Non Final Office Action mailed Aug. 24, 2005", 9 pgs.

"U.S. Appl. No. 10/081,170, Notice of Allowance mailed Sep. 18, 2006", 8 pgs.

"U.S. Appl. No. 10/081,170, Preliminary Amendment filed May 20, 2003", 2 pgs.

"U.S. Appl. No. 10/081,170, Preliminary Amendment filed Jun. 6, 2002", 1 pg.

"U.S. Appl. No. 10/081,170, Response filed Jan. 24, 2006 to Non Final Office Action mailed Aug. 24, 2005", 11 pgs.

"U.S. Appl. No. 10/081,170, Response filed Apr. 12, 2004 to Non Final Office Action mailed Jan. 15, 2004", 12 pgs.

"U.S. Appl. No. 10/081,170, Response filed Jun. 8, 2005 to Non Final Office Action mailed Feb. 8, 2005", 11 pgs.

"U.S. Appl. No. 10/081,170, Response filed Aug. 17, 2006 to Final Office Action mailed Apr. 12, 2006", 9 pgs.

"U.S. Appl. No. 10/081,170, Response filed Sep. 13, 2004 to Final Office Action mailed Jul. 13, 2004", 10 pgs.

"U.S. Appl. No. 10/081,170, Response filed Oct. 10, 2003 to Restriction Requirement mailed Sep. 10, 2003", 3 pgs.

"U.S. Appl. No. 10/081,170, Restriction Requirement mailed Sep. 10, 2003", 4 pgs.

"U.S. Appl. No. 12/113,690, Final Office Action mailed Apr. 14, 2011", 10 pgs.

"U.S. Appl. No. 12/113,690, Non-Final Office Action mailed Nov. 10, 2010", 11 pgs.

"U.S. Appl. No. 12/113,690, Preliminary Amendment filed Jul. 31, 2008", 14 pgs.

"U.S. Appl. No. 12/113,690, Response filed Jun. 23, 2011 to Final Office Action mailed Apr. 15, 2011", 17 pgs.

"U.S. Appl. No. 12/113,690, Response filed Aug. 5, 2010 to Restriction Requirement mailed Apr. 6, 2010", 14 pgs.

"U.S. Appl. No. 12/113,690, Response filed Dec. 22, 2010 to Non Final Office Action mailed Nov. 10, 2010", 19 pgs.

\* cited by examiner

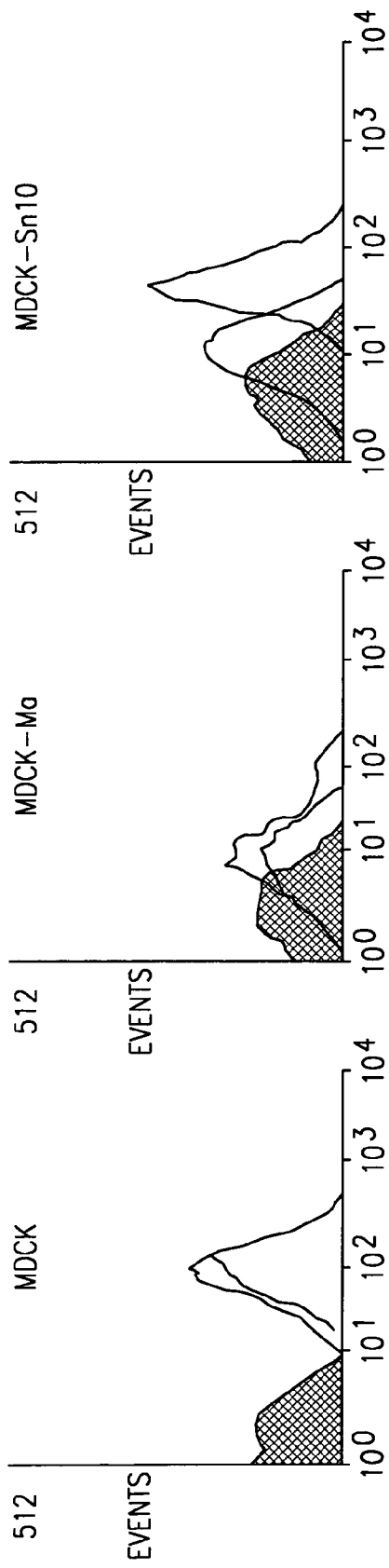
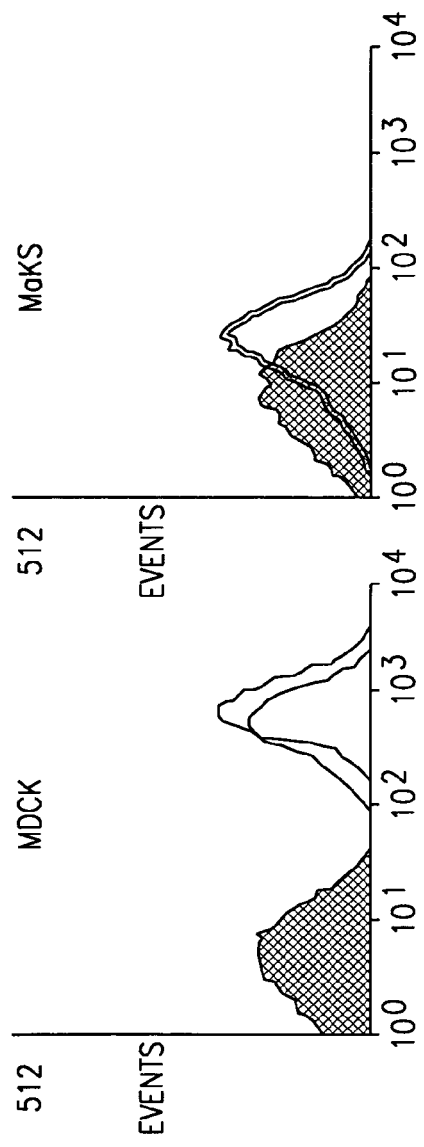

SEQUENCE LISTING

<160> NUMBER OF SEQ ID NOS: 6

<210> SEQ ID NO 1
<211> LENGTH: 24
<212> TYPE: DNA
<213> ORGANISM: Influenza A virus

<400> SEQUENCE: 1

```
tggctcgttt ctctcactat tgcc                                          24
```

<210> SEQ ID NO 2
<211> LENGTH: 26
<212> TYPE: DNA
<213> ORGANISM: Influenza A virus

<400> SEQUENCE: 2

```
ttatataggc atgagattga tgtccg                                        26
```

<210> SEQ ID NO 3
<211> LENGTH: 37
<212> TYPE: DNA
<213> ORGANISM: Influenza A virus

<400> SEQUENCE: 3

```
agcaaaagca ggggataatt ctattaacca tgaagac                            37
```

<210> SEQ ID NO 4
<211> LENGTH: 34
<212> TYPE: DNA
<213> ORGANISM: Influenza A virus

<400> SEQUENCE: 4

```
agtagaaaca aggtgttttt taattaatgc actc                               34
```

<210> SEQ ID NO 5
<211> LENGTH: 376
<212> TYPE: DNA
<213> ORGANISM: Artificial Sequence
<220> FEATURE:
<223> OTHER INFORMATION: A synthetic Influenza A virus mutant

<400> SEQUENCE: 5

```
atgaatccaa atcaaaagat aataacaatt ggctctgttt ctctcactat tgccacaata    60
tgcttcctta tgcaaattgc catcctggta actactgtaa cattgcattt caagcaacat   120
gagtgcaact ccccccccaaa caaccaagta atgctgtgtg aaccaacaat aatagaaaga   180
aacataacag atagtgtta ttgaaggcaa aagctgcatc aatcggtgct tttatgtgga   240
gttgataagg ggaaggaaac aggaaactga agtctggtgg acctcaaaca gtattgttgt   300
gttttgtggc acctcaggta catatggaac aggctcatgg cctgatgggg cggacatcaa   360
tctcatgcct atataa                                                  376
```

<210> SEQ ID NO 6
<211> LENGTH: 346
<212> TYPE: DNA
<213> ORGANISM: Artificial Sequence
<220> FEATURE:
<223> OTHER INFORMATION: A synthetic Influenza A virus mutant

<400> SEQUENCE: 6

```
atgaatccaa atcaaaagat aataacaatt ggctctgttt ctctcactat tgccacaata    60
tgcttcctta tgcaaattgc catcctggta actactgtaa cattgcattt taaataggca   120
agtcatagtt gacagaggta atagatccgg ttattctggt attttctctg ttgaaggcaa   180
aagctgcatc aatcggtgct tttatgtgga gttgataagg ggaaggaaac aggaaactga   240
agtctggtgg acctcaaaca gtattgttgt gttttgtggc acctcaggta catatggaac   300
aggctcatgg cctgatgggg cggacatcaa tctcatgcct atataa                  346
```

MUTANT CELLS WITH ALTERED SIALIC ACID

CROSS-REFERENCE TO RELATED APPLICATIONS

This application is a divisional of U.S. patent application Ser. No. 10/081,170, filed Feb. 22, 2002, now U.S. Pat. No. 7,176,021, which application claims the benefit of the filing date of U.S. Provisional Application Ser. No. 60/271, 044, filed on Feb. 23, 2001, the disclosure of which is incorporated by reference herein.

STATEMENT OF GOVERNMENT RIGHTS

The invention was made, at least in part, with a grant from the Government of the United States of America (grant AI44386 and AI33898 from the National Institutes of Health). The Government has certain rights in the invention.

BACKGROUND OF THE INVENTION

Influenza A viruses possess two surface spike proteins, hemagglutinin (HA) and neuraminidase (NA) (Lamb et al., 1996). The HA protein, a trimeric type I membrane protein, is responsible for binding to sialyloligosaccharides (oligosaccharides containing terminal sialic acid linked to galactose) on host cell surface glycoproteins or glycolipids (reviewed Wiley et al., 1987). This protein is also responsible for fusion between viral and host cell membranes, following virion internalization by endocytosis. Neuraminidase (NA), a tetrameric type II membrane protein, is a sialidase that cleaves terminal sialic acid residues from the glycoconjugates of host cells and the HA and NA, and thus is recognized as receptor-destroying enzyme (Air et al., 1989). This sialidase activity is necessary for efficient release of progeny virions from the host cell surface, as well as prevention of progeny aggregation due to the binding activity of viral HAs with other glycoproteins (Pause et al., 1974; Shibata et al., 1993). Thus, the receptor-binding activity of the HA and the receptor-destroying activity of the NA likely act as counterbalances, allowing efficient replication of influenza virus, e.g., influenza A virus.

Influenza A viruses of all known subtypes have been isolated from a variety of animals, including humans, wild and domestic birds, pigs, horses, and sea mammals (Webster et al., 1992). Viruses responsible for the 1957 and 1968 influenza pandemics were reassortants between human and avian viruses, with the PB1, HA and/or NA genes derived from the latter (Kawaoka et al., 1989; Laver et al., 1973; Scholtissek et al., 1978). Such interspecies transmission of avian virus genes forces adaptation of the gene products to the new environment (i.e., human respiratory organs).

Comparative studies have demonstrated that HA receptor specificity differs among influenza A viruses, depending on the animal species from which they were isolated (Rogers et al., 1983a; Rogers et al., 1983b). Thus, amino acids alterations are likely needed for efficient viral growth in new animal hosts. However, it is unclear if HA mutations alone, or in addition to mutations in HA, are needed for influenza virus adaptation in new hosts.

Thus, what is needed is a method to select for influenza virus mutants capable of replicating in an altered host cell.

SUMMARY OF THE INVENTION

The invention provides an isolated mutant vertebrate cell which has altered expression of sialic acid containing host cell receptors for influenza virus, and methods of preparing and using the mutant cell. The mutant cell preferably comprises decreased levels of sialic acid containing host cell receptors relative to a corresponding wild-type cell which supports efficient influenza virus replication, i.e., the cell is not a CHO cell. The decreased levels of sialic acid containing host cell receptors in the mutant cell of the invention is not the result of exogenous sialidase treatment but rather the result of endogenous alterations in the mutant cell. Thus, a mutant cell of the invention is one which, in the absence of exogenous sialidase, comprises decreased levels of sialic acid relative to the levels of sialic acid in a corresponding wild-type cell. Cells which support efficient influenza virus replication include, but are not limited to, mammalian cells such as simian cells, for instance, African green monkey cells (e.g., Vero cells), CV-1 cells, and rhesus monkey kidney cells (e.g., LLcomk.2 cells), canine cells (e.g., MDCK cells), bovine cells (e.g., MDBK cells), swine cells, ferret cells (e.g., mink lung cells), BK-1 cells, human cells, and avian cells including embryonic fibroblasts.

Thus, the present invention provides mutant cells useful to propagate influenza virus having reduced or decreased sialidase activity. The mutant cell is preferably obtained (derived), e.g., by selection, from a continuous cell line or strain of cultured mammalian or avian cells in which influenza virus efficiently replicates and which line or strain has substantially wild-type levels of sialic acid containing receptors for influenza virus (a "wild-type" cell). In one embodiment, the mutant cell has at least 2, 3, 5, 7, or 10, or more, e.g., 12, 15 or 20, fold lower levels of one or more different types of sialic acid relative to the corresponding wild-type cell.

To isolate a mutant cell of the invention, e.g., a cell having decreased or reduced sialic acid content, a population of cells which are permissive for influenza virus replication and sensitive to growth inhibition by an agent, e.g., a lectin or an agglutinin, is contacted with an amount of the agent that specifically binds to sialic acid or otherwise inhibits sialic acid production, thereby inhibiting cell growth, so as to yield proliferating cells that are resistant to growth inhibition by the agent. Then an agent-resistant cell is isolated. For example, in one embodiment, the isolated mutant cell of the invention has decreased levels of N-acetylneuraminic acid. In another embodiment, the isolated mutant cell has decreased levels of N-glycolylneuraminic acid. In yet another embodiment, the isolated mutant cell has decreased levels of N-glycolylneuraminic acid and N-acetylneuraminic acid. Preferred growth inhibiting agents include, but are not limited to, lectins such as *Maakia amurensis* lectin, *Sambucus nigra* lectin, and *Tritrichomonas mobilensis* lectin, and agglutinins such as *Limax flavus* agglutinin. However, it is also envisioned that agents other than lectins or agglutinins may be employed to isolate a mutant cell of the invention. For example, a population of cells which are permissive for influenza virus replication, is contacted with an amount of an agent that inhibits sialic acid containing host cell receptor synthesis, e.g., inhibits receptor biosynthetic enzymes, so as to yield cells having decreased levels of sialic acid containing host cell receptors. Preferably, the agent is one which selects for cells having decreased levels of receptors and/or selects against cells having substantially wild-type levels of receptors.

As described hereinbelow, cell lines were generated that expressed reduced levels of the influenza viral receptor determinant, sialic acid, by selecting Madin-Darby canine kidney cells which were resistant to a lectin specific for sialic acid linked to galactose by α(2-3) or α(2-6) linkages. One of these cell lines, MaKS, had less than 1/10 as much N-acetylneuraminic acid as its parental cell line, MDCK. When serially passaged in MaKS, human H3N2 viruses lost sialidase activity due to a large internal deletion in the NA gene, without alteration of the HA gene. These findings indicate that NA mutations can contribute to the adaptation of influenza A virus to new host environments and hence may play a role in the transmission of virus across species.

Also provided is a method of using a mutant cell isolated by selecting for a cell having decreased levels of sialic acid containing host cell receptors for influenza virus. The method comprises contacting a mutant cell of the invention with an influenza virus which specifically binds receptors present on the mutant cell, e.g., receptors that are present on the mutant cell in decreased levels or amounts relative to a corresponding wild-type cell, to obtain progeny virus. Progeny virus then is serially propagated in the mutant cell, e.g., the progeny viruses are adapted for efficient replication in the mutant cell.

The invention further provides a method of propagating influenza viruses having reduced sialidase activity. The method comprises contacting a mutant cell of the invention with an influenza virus having reduced sialidase activity, which virus specifically binds receptors on the mutant cell, so as to yield progeny viruses.

Thus, the mutant cell of the invention is useful for propagating influenza viruses with reduced sialidase activity, e.g., due to mutations in the viral NA gene, and to select for those viruses. Viruses obtained by the methods of the invention may be employed in vaccines, to prepare monoclonal or polyclonal antibodies specific for those viruses, to prepare recombinant or reassortant viruses, or for gene delivery including the delivery of immunogenic non-influenza virus proteins or peptide for vaccines or therapeutic proteins. Thus, the present invention also provides vaccine compositions comprising at least one influenza virus obtained by the methods of the invention, or recombinant or reassortant viruses derived therefrom, in inactivated or attenuated form, optionally further comprising at least one of: (a) at least one pharmaceutically acceptable carrier or diluent; (b) at least one adjuvant and/or (c) at least one viral chemotherapeutic agent. The at least one carrier, diluent, adjuvant or chemotherapeutic agent enhances an immune response to the virus in a mammal administered the vaccine composition.

The present invention also provides a method for eliciting an immune response to an influenza virus obtained by the methods of the invention, or recombinant or reassortant viruses derived therefrom, in a mammal, which response is prophylactic or therapeutic for an influenza virus infection. The method comprises administering to the mammal a vaccine composition comprising an inactivated and/or attenuated influenza virus of the present invention. The composition is provided in an amount that is protective or therapeutic for the mammal against a clinical influenza virus pathology caused by infection with at least one influenza A or B virus strain.

BRIEF DESCRIPTION OF THE FIGURES

FIGS. 1A-E. Binding of lectin-resistant cell lines. For each cell line, cells were incubated with digoxigenin-labeled *Maakia amurensis* (MAA) lectin or *Sambucus nigra* (SNA) lectin, followed by fluorescein isothiocyanate-labeled anti-digoxigenin antibody, and then analyzed by FACS. A) MDCK cells incubated with labeled MAA lectin or labeled SNA lectin; B) MDCK-Ma cells incubated with labeled MAA lectin or labeled SNA lectin; C) MDCK Sn10cells incubated with labeled MAA lectin or labeled SNA lectin; D) MDCK cells incubated with labeled MAA lectin or labeled SNA lectin; and E) MaKS cells incubated with labeled MAA lectin or labeled SNA lectin. Bold lines, binding of the MAA lectin; narrow lines, binding of the SNA lectin; shaded profiles, negative control (no lectin added).

DETAILED DESCRIPTION OF THE INVENTION

Figure 2A:
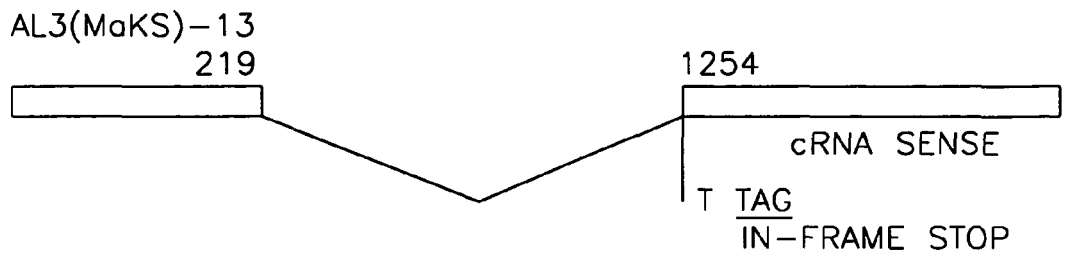
FIGS. 2A-B. Structures of the NA genes of the AL3 (MaKS)-13 and K4(MaKS)-I 3 mutants. (A) The AL3 (MaKS)-I 3 contains a 936-nucleotide deletion (from bases 220 to 1253) that removes a large portion of the NA gene coding sequence. This mutation also brings a TAG stop codon into frame two bases beyond the deletion, so that the gene encodes a 66-amino-acid peptide, corresponding to the cytoplasmic tail, transmembrane region, stalk, and a portion of the head of NA. (B) The K4(MaKS)-13 NA gene contains a 1,066-nucleotide deletion (from bases 130 to 1193) that removes a large portion of the NA gene coding sequence. This mutation brings a TAG stop codon into frame four bases beyond the deletion, so that the gene encodes a 38-amino-acid peptide, corresponding to the cytoplasmic tail and transmembrane region of the NA gene.

As used herein, the terms "isolated and/or purified" refer to in vitro preparation, isolation and/or purification of a cell or influenza virus of the invention, so that it is not associated with in vivo substances, or is substantially purified from in vitro substances. As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 50 percent, more preferably more than about 80 percent of all macromolecular species present in the composition, and even more preferably more than about 85%, about 90%, about 95%, and about 99%. Most preferably, the object species is purified to essential homogeneity (contaminant species cannot be detected in the composition by conventional detection methods).

The phrase "efficient replication" in the context of the present invention, is defined as producing high infectivity titers in in vitro tissue culture systems, such as $10^4$-$10^{10}$ PFU/ml, and preferably $10^6$-$10^9$ PFU/ml. The screening of influenza viruses for replication or use in vaccine production, can be assayed using any known and/or suitable assay, as is known in the art. Such assays (alone or in any combination) that are suitable for screening include, but are not limited to, viral replication, quantitative and/or qualitative measurement of inactivation (e.g., by antisera), transcription, replication, translation, virion incorporation, virulence, HA or NA activity, viral yield, and/or morphogenesis, using such methods as reverse genetics, reassortment, complementation, and/or infection. For example, virus replication assays can be used to screen for attenuation or inactivation of the virus. See, e.g., Krug, R. M., ed., The Influenza Viruses, Plenum Press, New York, (1989).

"Sialic acid" refers to a family of amino sugars containing 9 or more carbon atoms, e.g., N- and O-substituted derivatives of neuraminic acid.

Influenza Virus Replication

Influenza A viruses possess a genome of eight single-stranded negative-sense viral RNAs (vRNAs) that encode a total of ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs.

Cell Lines and Influenza Viruses that can be Used in the Present Invention

According to the present invention, any cell which supports efficient replication of influenza virus can be employed to prepare a mutant cell of the invention. The mutant cells of the invention express reduced or decreased levels of one or more sialic acids which are receptors for influenza virus, preferably an influenza type A or B virus, and may be employed to select for mutant influenza virus strains having decreased sialidase activity which are adapted for efficient replication in the cells. The adapted virus can be made into a reassortant virus, or a recombinant virus, e.g., one or more segments of the viral genome of the adapted virus, such as the NA segment, may be cloned via reverse genetics and used to prepare recombinant influenza virus (e.g., see WO 00/60050).

In one embodiment, the mutant cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The adapted virus is preferably purified by a process that has been shown to give consistent results, before being inactivated or attenuated for vaccine production (see, e.g., World Health Organization, 1982).

It is preferred to establish a complete characterization of the cells to be used, so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the adapted virus produced in the mutant cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

The host cells of the invention are useful to prepare influenza virus-based vaccines, e.g., a vaccine in which influenza virus is a vaccine vector for non-influenza virus pathogens, e.g., pathogens such as lentiviruses, e.g., HIV, hepatitis B virus, hepatitis C virus, herpes viruses, e.g., HSV or CMV, rhinovirus, filoviruses, foot and mouth disease virus, and for pathogens which are associated with malaria, but may also be useful in gene therapy vectors, e.g., for cancer, AIDS, adenosine deaminase, muscular dystrophy, ornithine transcarbamylase deficiency and central nervous system tumors.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); Webster et al., 1977); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines.

Inactivated influenza virus vaccines of the invention are provided by inactivating virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

Live Attenuated Virus Vaccines.

Live attenuated influenza virus vaccines, using the adapted virus of the invention, can also be used for preventing or treating influenza virus infection, according to known method steps. Attenuation is preferably achieved in a single step by transfer of attenuated genes from an attenuated donor virus to an isolate or reassorted virus according to known methods (see, e.g., Murphy, 1993).

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or a high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions for Vaccine or Gene Therapy

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; Goodman et al., 1990; Avery's Drug Treatment, 1987; Osol, 1980; Katzung, 1992.

The composition of the invention is generally presented in the form of individual doses (unit doses).

Conventional vaccines generally contain about 0.1 to 200 μg, preferably 10 to 15 μg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Goodman et al., 1990; Avery's, 1987; Osol, 1980; and Katzung, 1992.

When a composition of the present invention is used for administration to an individual, it can further comprise salts, buffers, adjuvants, or other substances which are desirable for improving the efficacy of the composition. For vaccines, adjuvants, substances that augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza viruses, using techniques known in the art.

A pharmaceutical composition according to the present invention may further or additionally comprise at least one chemotherapeutic compound, e.g., for gene therapy, an immunosuppressant, an anti-inflammatory agent or an immunostimulatory agent, or anti-viral agents including, but not limited to, gamma globulin, amantadine, guanidine, hydroxybenzimidazole, interferon-α, interferon-β, interferon-γ, tumor necrosis factor-α, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir. See, e.g., Katzung (1992), and the references cited therein on pages 798-800 and 680-681, respectively.

The composition can also contain variable but small quantities of endotoxin-free formaldehyde, and preservatives, which have been found safe and not contributing to undesirable effects in the organism to which the composition of the invention is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom of influenza viral infection becomes manifest. The prophylactic administration of the composition serves to prevent or attenuate any subsequent infection. When provided therapeutically, the attenuated or inactivated viral vaccine is provided upon the detection of a symptom of actual infection. The therapeutic administration of the compound(s) serves to attenuate any actual infection. See, e.g., Berkow et al., 1992; Goodman et al., 1990; Avery, 1987; and Katzung, 1992. An attenuated or inactivated vaccine composition of the present invention may thus be provided either before the onset of infection (so as to prevent or attenuate an anticipated infection) or after the initiation of an actual infection.

Similarly, for gene therapy, the composition comprising an adapted virus comprising a therapeutic gene may be provided before any symptom of a disorder or disease is manifested, or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, for instance, for a vaccine, the administration of the composition to an organism that enhances at least one primary or secondary humoral or cellular immune response of that organism against at least one strain of an infectious influenza virus.

The "protection" provided need not be absolute, e.g., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A vaccine of the present invention may confer resistance to one or more influenza strains by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

In a second embodiment, the vaccine is provided to a mammalian female (at or prior to pregnancy or parturition), under conditions of time and amount sufficient to cause the production of immune responses which serve to protect both the female and the fetus or newborn (via passive incorporation of the antibodies across the placenta or in the mother's milk).

The present invention thus includes methods for preventing or attenuating a disease or disorder, e.g., infection by at least one influenza virus strain. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; Goodman et al., 1990; Avery, 1987; and Katzung, 1992.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a vaccine composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Goodman et al., 1990; Avery's, 1987; Ebadi, 1985; and Katsung, 1992.

The dosage of an attenuated virus vaccine for a mammalian (e.g., human) or avian adult can be from about $10^3$-$10^7$ plaque forming units (PFU)/kg, or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg, per component for older children ≥3 years of age, and 7.5 µg per component for older children <3 years of age. The quantity of NA can also be standardized, however, this glycoprotein can be labile during the processor purification and storage (Kendal et al., 1980; Kerr et al., 1975). Each 0.5-ml dose of vaccine preferably contains approximately 1-50 billion virus particles, and preferably 10 billion particles.

The invention will be further described by the following non-limiting example.

EXAMPLE

Materials and Methods

Viruses and cells. Human H3N2 viruses isolated from a single patient, either in embryonated chicken eggs (A/Tottori/AT1/AM2AL3/94; AM1AL3) of Madin-Darby canine kidney (MDCK) cells (A/Tottori/872/K4/94; K4), were obtained from T. Ito (Tottori University, Tottori, Japan). Virus stocks were grown either in 10 day-old embryonated chicken eggs (AMZAL3 virus) or on MDCK cells (K4 virus) in minimal essential medium (MEM) supplemented with 0.3% bovine serum albumin and 0.5 mg of trypsin/ml. MDCK cells were maintained in MEM supplemented with 5% newborn calf serum (Sigma, St. Louis, Mo.).

Generation of lectin-resistant cell lines. MDCK cells grown to 75% confluency were washed three times with phosphate-buffered saline and incubated with *Maakia amurensis* (MAA) lectin (100 mg/ml; Boehringer Mannheim, Mannheim, Germany) or *Sambucus nigra* (SNA) lectin (100 mg/ml; Boehringer Mannheim) in MEM containing 0.3% bovine serum albumin. After a 48 hour incubation, the medium was replaced with growth medium (MEM-5% fetal calf serum). Lectin selection was repeated as above two additional times. Surviving cell colonies were then cloned, and the SNA- and MAA-selected cell lines were designated MDCK-Sn10 and MDCK-Ma, respectively.

Fluorometric HPLC method for determination of sialic acid content. The sialic acid (N-acetylneuraminic acid [NeuAc] and N-glycolylneuraminic acid [NeuGc]) content of both cell lines and the purified virus was determined fluorometrically by high-performance liquid chromatography as described in Suzuki et al. (1997). Each sample was placed in a 5-ml ground glass-topped vial and mixed with 100 µl (25 mM) of sulfuric acid. The vials were then heated at 60° C. for 12 hours to hydrolize sialo-sugar chains. After cooling, 50 µl of 1,2-diamino-4,5-methylene dioxybenzene was added to 50 µl of the hydrolyte, and the mixture was heated to 60° C. for 2.5 hours in the dark to develop the fluorescence of the sialic acid. A 10 µl aliquot of the resulting solution was then injected into an 880-PU high performance liquid chromatograph (JASCO, Tokyo Japan) equipped with a sample injector valve (model 7125; Reodyne) and a fluorescent spectrophotometer (650-105; Hirachi, Tokyo, Japan) with a 20-µl flow cell and a recorder (Chromatopac C-RSA; Shionadzu, Kyoto, Japan). The fluorescence spectrophotometer was positioned at an excitation wavelength of 373 nm and an emission wavelength of 448 nm. Standard mixtures (200 pmol/µl) of NeuAc (Sigma) and NeuGc (Sigma) were used to establish calibration curves.

Fluorometric sialidase activity assay. Virus sialidase activity ($5 \times 10^5$ PFU) was measured with 2'-(4-methylumbelliferyl)-α-D-N-acetylneuraminic acid (Sigma) as a substrate as described in Hara et al. (1987). Briefly the fluorogenic substrate, dilute 1:2 with 0.5 M sodium acetate (pH 4.6), was added to an equal volume of virus samples and incubated for 30 minutes at 37° C. Reactions were stopped with 200 ml of 0.5 M $Na_2CO_2$ (pH 10.7), and fluorescence was then incubated at an excitation wavelength of 360 nm and an emission wavelength of 460 nm. All reactions were performed in duplicate.

Sequence analysis of the NA and HA genes. Total viral RNA (vRNA) was obtained from virus sample with use of the Qiappin vRNA purification kit as instructed by the manufacturer (Qiagen, Inc., Valencia, Calif.). For cDNA production, the oligonucleotide Uni-12, complementary to the conserved 12 vRNA 3' terminal nucleotides of influenza A virus gene segments was used as a primer for the Moloney Murine Leukemia Virus reverse transcriptase (Promega, Madison, Wis.) reaction. The NA gene cDNA was amplified during 30 rounds of PCR with the NA gene-specific primers JN2-43 (5' cRNA sense sequence: 5'-TGGCTCGTTTCTCTCACTATTGCC-3'; SEQ ID NO:1) and JN2-1410r (3'-cRNA antisense sequence: 5'-TTATATAGGCATGAGATTGATGTCCG-3'; SEQ ID NO:2) and 10 U of Pwo DNA polymerase (Boehringer Mannheim). The resulting PCR products were subcloned into the vector pCR21 (Invitrogen, Carlsbad, Calif.) and used for automated fluorescent sequencing. The HA gene were cloned in a similar fashion with the HA gene-specific primers JH3-Up (5' cRNA sense primer sequence, 5'-AGCAAAAGCAGGGGATAATTCTATTAACCATGAAGAC-3'; SEQ ID NO:3) and JH3-Down (3' cRNA antisense primer sequence 5'-AGTAGAAACAAGGGTGTTTTTAATTAATGCACTC-3'; SEQ ID NO:4). For each isolate, three clones were examined to obtain a NA and HA consensus sequences. The sequence

```
for AL3 (MaKS)-13 is
ATGAATCCAAATCAAAAGATAATAACAATTGGCTCTGTTTCTCTCACTAT

TGCCACAATATGCTTCCTTATGCAAATTGCCATCCTGGTAACTACTGTAA

CATTGCATTTCAAGCAACATGAGTGCAACTCCCCCCCAAACAACCAAGTA

ATGCTGTGTGAACCAACAATAATAGAAAGAAACATAACAGAGATAGTGTA

TTGAAGGCAAAAGCTGCATCAATCGGTGCTTTTATGTGGAGTTGATAAGG

GGAAGGAAACAGGAAACTGAAGTCTGGTGGACCTCAAACAGTATTGTTGT

GTTTTGTGGCACCTCAGGTACATATGGAACAGGCTCATGGCCTGATGGGG

CGGACATCAATCTCATGCCTATATAA; SEQ ID NO:5);
and for K4(MaKS)-13 is
ATGAATCCAAATCAAAAGATAATAACAATTGGCTCTGTTTCTCTCACTAT

TGCCACAATATGCTTCCTTATGCAAATTGCCATCCTGGTAACTACTGTAA

CATTGCATTTTAAATAGGCAAGTCATAGTTGACAGAGGTAATAGATCCGG

TTATTCTGGTATTTTCTCTGTTGAAGGCAAAAGCTGCATCAATCGGTGCT

TTTATGTGGAGTTGATAAGGGGAAGGAAACAGGAAACTGAAGTCTGGTGG

ACCTCAAACAGTATTGTTGTTTTGTGGCACCTCAGGTACATATGGAAC

AGGCTCATGGCCTGATGGGCGGACATCAATCTCATGCCTATATAA;

SEQ ID NO:6).
```

Results

Generation of lectin-resistant cell lines. To produce cell lines with a decreased level of sialic acid expression on the cell surface, two lectins were used, SNA and MAA, that differ in sialic acid-binding specificity. The MAA lectin binds to sialic acid linked to galactose by α(2,3) linkages (Wang et al., 1988), while the SNA lectin is specific for sialic acids linked to galactose or N-acetylgalactosamine by α(2-6) linkages (Shibuya et al., 1987). The MDCK cell line, which supports the growth of influenza viruses, was used as a parent cell for lectin selection. When incubated in the presence of either lectin, the majority of cells died within a week. Resistant cell clones were then grown out for stock cultures. The cell lines resulting from MAA and SNA lectin selection were designated MDCK-Ma and MDCK-Sn10, respectively.

Fluorescent-activated cell sorting (FACS) with digoxigenin-labeled MAA and SNA lectins (FIG. 1A) demonstrated high levels of binding of MDCK cells to both lectins, as previously reported (Ito et al., 1997). MDCK-Sn10 cells, selected with α(2,6) linkage-specific lectin, retained strong binding to the α(2,3) specific MAA lectin but showed SNA lectin binding weaker than that of the MDCK parent. By contrast, MDCK-Ma cells, selected with the α(2-3) linkage-specific lectin, bound both lectins much more weakly than MDCK cells.

Viral growth in MDCK-Sn10 and MDCK-Ma cell lines. To learn how influenza viruses adapt to cells with reduced receptor expression, two influenza virus variants (AM2AL3 and K4) were chosen with known sialic acid receptor linkage specificity (Ito et al., 1997). The K4 virus specifically recognizes NeuAc linked to galactose by α(2-6) linkages [NeuAcα(2-6)Gal], while the AM2AL3 virus is specific for NeuAcα(2-3)Gal. Both viruses replicated almost as well in MDCK-Sn10 cells as in MDCK cells (Table 1). However, the titers of both viruses in MDCK-Ma cells were 1 log lower than in MDCK cells. Also, after infection with either virus, even at a multiplicity of infection of 10, a small percentage of MDCK-Ma cells continued to grow to confluency without any cytopathic effects. Virus production could not be detected in these surviving cells by hemagglutination assay upon replacement of the medium with that containing trypsin, which promotes virus growth. The cells were also negative by immunochemical staining for both influenza virus HA and NP proteins (data not shown), thus demonstrating that the cells were not persistently infected. The surviving cells were designated MaKS.

TABLE 1

Replication of influenza viruses in lectin-resistant cell lines*

| Cell line | Titer ($TCID_{50}$/ml) | |
|---|---|---|
| | AM2AL3 | K4 |
| MDCK | $1.8 \times 10^9$ | $5.6 \times 10^4$ |
| MDCK-Sn10 | $5.6 \times 10^8$ | $3.2 \times 10^4$ |
| MDCK-Ma | $1.8 \times 10^8$ | $5.6 \times 10^3$ |

*The susceptibility of each cell line was determined by infecting cells with AM2AL3 or K4 with virus and determining the dose required to infect 50% of tissue culture cells ($TCID_{50}$).

FACS analysis with both SNA and MAA lectins demonstrated that the MaKS cells, like the MDCK-Ma cells from which they were derived, bound the α(2,6)-specific SNA lectin much more weakly than did MDCK cells (FIG. 1B). In addition, the MAA lectin-binding peak of MaKS cells was much narrower than that of the MDCK-Ma cell line, with loss of a small shoulder peak representing a higher MAA-binding population (FIG. 1).

To determine whether reduced amounts of sialic acid were responsible for the reduced lectin binding of MaKS cells, the sialic acid levels present in the MaKS cells were quantified by liquid chromatographic analysis. The MaKS cell line showed much lower levels of both NeuAc and NeuGc (8.2 and 0.4 pmol/μg of protein, respectively) than MDCK cells (216.0 and 2.5 pmol/μg protein), although the NeuGc content was much lower. These data demonstrate an extensive reduction of sialic acid receptor determinant in MaKS cells.

Adaptation of virus in MaKS cells. To determine how AM2AL3 and K4 viruses propagate and adapt to growth in cells expressing very low levels of virus receptor, both viruses were serially passaged in MaKS cells in liquid culture. Since both viruses replicated more poorly in MaKS cells than in MDCK cells (Table 2), passages 1 through 3 were performed without dilution, and passages 4 through 13 were performed at 1:1,000 dilution. After passage 8, the diameter of plaques produced by either variant had changed from large (greater than 3 mm) to smaller (approximately 1 nm). By passage 10 and higher, only smaller plaques were present when the viruses were assayed with MDCK cells (data not shown). After 13 serial passages, both viruses were able to grow in MaKS cells as well as or better than in MDCK cells (Table 2). Virus stocks produced from either variant after passage 13 were amplified and designated AL3(MaKS)-13 and K4(MaKS)-13, respectively.

TABLE 2

Replication of viruses adapted to growth in lectin-selected cells*

| Cell line | Titer (TCID$_{50}$/ml) | | | |
|---|---|---|---|---|
| | AM2AL3 | AL3(MaKS)-13 | K4 | K4(MaKS)-13 |
| MDCK | $1.8 \times 10^9$ | $5.6 \times 10^4$ | $5.6 \times 10^4$ | $5.6 \times 10^4$ |
| MaKS | $5.6 \times 10^6$ | $5.6 \times 10^4$ | $1.8 \times 10^3$ | $1.8 \times 10^3$ |
| Resin, MDCK titer/MaKS titer | 321 | 1 | 31 | 0.3 |

*The susceptibility of each cell line was determined by infecting cells with AM2AL3 (grown in eggs), K4 (grown in MDCK cells). AL3(MaKS)-13 (grown in MaK3 cells), or K4(MaKS)-13 (grown in MaKs cells) stock virus and determining the dose required to infect 50% of tissue culture cells(TCID$_{50}$). Note that both viruses adapted in MaKS cells grow in these cells as well as [AL3(MaKS)-13] or better than [K4(MaKS)-13] in MDCK cells, while the original viruses grow better in MDCK cells.

Mutational analysis of the HA and NA genes of AL3 (MaKS)-13 and K4(MaKS)-13 viruses. To determine the molecular basis of virus adaptation to a cellular environment characterized by a reduced receptor concentration, the HA genes of the AL3(MaKS)-13 and K4(MaKS)-13 viruses were reverse transcribed, the cDNAs amplified by PCR, and the resulting products sequenced. Neither of the genes contained mutations by comparison with the corresponding HA genes from the two parental viruses.

Figure 2B:
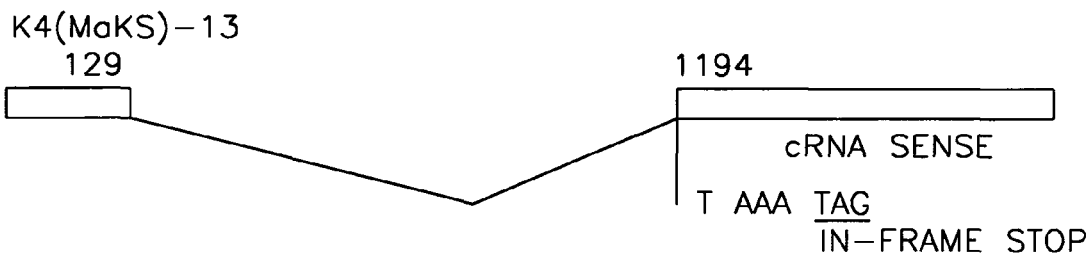

Since changes in NA sialidase activity likely influence HA receptor-binding activity, the NA sequence of the AL3 (MaKS)-13 and K4(MaKS)-13 viruses was determined. Sequence analysis of the NA genes of both variants revealed large internal deletions (FIG. 2). In AL3(MaKS)-13, the deletion extended from nucleotides 220 to 1253, shifting a reading frame and thus generating a stop codon immediately after the deletion. The coding capacity of this NA is 66 amino acids, corresponding to the cytoplasmic tail, the transmembrane domain, stalk region, and a short portion of the head region of NA. Similarly, the K4(MaKS)-13 isolate contained a deletion in the NA gene from bases 130 to 1193, bringing a stop codon into frame at codon 39. Like the AL3(MaKS)-13 virus, the gene no longer encoded a full catalytic head region. Thus, viruses passaged in a cell line with very low receptor expression lost their NA catalytic activity.

Figure 3:
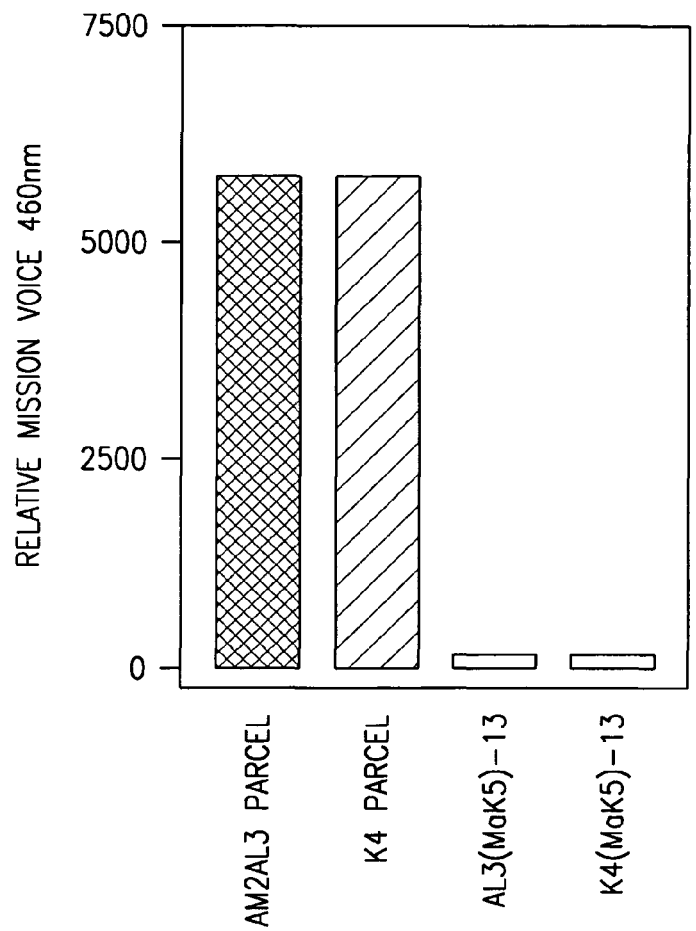
FIG. 3. Sialidase activity of the parental AM2AL3 and K4 viruses and the AL3(MaKS)-13 and K4(MaKS)-13 mutants. For each sample, virus ($5 \times 10^2$ PFU) was incubated in duplicate for 1 hour at 37° C. in the presence of a fluorogenic sialidase substrate (4-methylumbelliferyl-$\alpha$-N-acetyl-neuraminic acid). The fluorescence of released 4-methylumbelliferone was determined with a fluorometer (Labsystems Fluoroskan II) with excitation at 360 nm and emission at 460 nm.

To confirm this result, the AL3(MaKS)-13 and K4 (MaKS)-13 variants were analyzed for sialidase activity, using a fluorescent sialidase substrate [2'(4-methylumbelliferyl)-α-D-N-acetylneuraminic acid]. Unlike the parental viruses, neither of the NA deletion mutants had detectable sialidase activity (FIG. 3).

Extent of sialylation of viral glycoproteins. During normal infection, viruses with reduced sialidase activity fail to grow efficiently and aggregate at the cell surface (Palese et al., 1974; Shibata et al., 1993). Why, then, do AL3(MaKS)-13 and K4(MaKS)-13 viruses, which lack sialidase activity, grow in MaKS cells? One possible explanation would be that since the sialic acid content of these cells is low, the extent of sialylation of the HA and NA oligosaccharides may also be low, preventing the aggregation of viruses at the infected cell surface, even when viral sialidase activity is absent. To test this hypothesis, the sialic acid content in purified virus preparations was compared between AM2AL3 and K4 viruses grown in MDCK cells and AL3(MaKS)-13 virus grown in MaKS cells. The NeuAc content was similar among the virus samples, although the AM2AL3 virus had lower sialic acid content (0.9 pmol of NeuAc/g of protein) than the other samples (A/Tottori/872/K4/94, 3.8 pmol of NeuAc/g of protein; AL3(MaKS)-13, 2.6 pmol of NeuAc/g of protein).

Thus, viruses lacking sialidase activity can grow efficiently in cells expressing a reduced level of sialic acid because the viral glycoproteins are not sialylated extensively compared with those in normal cell lines and are not bound by the HA, thus preventing viral aggregation.

Discussion

In previous studies, the passage of influenza A viruses in the presence of an exogenous bacterial sialidase activity and antibodies to the viral NA led to deletion of the viral NA gene (Liu et al., 1993; Liu et al., 1995; Yang et al., 1997). Moreover, NA mutants obtained by such passaging were able to grow in cell cultures lacking exogenous sialidase activity, as well as in eggs and mice, as a result of compensatory mutations in the HA protein that reduce the molecule's affinity for sialic acid residues (Hughes et al., 2000). As described herein, influenza A viruses can adapt to growth in cells with greatly reduced receptor expression by large NA gene deletion mutations that abolish sialidase activity. Even though the reduction of viral receptors could theoretically affect the receptor-binding HA protein, only the NA gene was altered.

What is the molecular basis of this finding? In normal cellular environments where sialic acid receptors are abundant, the loss of NA activity can be compensated for by reduction of the viral HA affinity for sialic acid, allowing efficient release of progeny from the host cell surface and preventing virion aggregation (Hughes et al., 2000). In the absence of high levels of viral receptors, as in our MaKS cells, a reduction of HA affinity is not necessary to release viral progeny and allow the growth of NA deletion mutants. In fact, high-affinity binding of the HA protein must be maintained for viral replication in cells expressing low levels of viral receptor. Sialidase activity, however, is not required for virion release and prevention of virion aggregation in such an environment, since the amounts of sialic acid on cell surface molecules are quite low and the sialic acid contents of NA deletion virions are similar to that of wild-type virions. In fact, sialidase activity is likely deleterious for viral growth because it further removes receptor determinant sialic acid from the cell surface. Recently, it was shown that influenza A virus lacking a NA stalk, and thus unable to grow in eggs, acquired a stalk insertion of up to 22 amino acids through nonhomologous RNA-RNA recombination (Mitnaul et al., 2000). Taken together, these finding indicate that influenza viruses can adapt to new host environments by undergoing radical genetic changes, including large insertions and deletions.

In both this and previous studies (Hughes et al., 2000; Liu et al., 1993), viruses lost sialidase activity by internal deletions in the NA gene segment that spared segment ends encoding the cytoplasmic tail and transmembrane region. Thus, the preserved regions of the NA gene in these mutants may be necessary for functions such as virion morphogenesis and stability.

MaKS cells have a lower sialic acid content than their parental (MDCK) cells. Although similar cell lines have been produced from CHO cells (Ray et al., 1991), they have not proven useful for influenza virus studies because of their inability to support efficient influenza virus. By contrast, MaKS cells were derived from MDCK cells, a standard cell line in studies of influenza viruses, and should be useful in viral receptor-based analyses. For example, since exogenously added gangliosides are known to be incorporated into host cell membranes (Carroll et al., 1985), one could therefore incubate known gangliosides with MaKS cells and test their ability to serve as viral receptors.

During the past century, three influenza A virus pandemics arose when the HA or both the HA and NA genes of emerging viruses were introduced into a human population. Comparative studies of viruses from different host animals suggest that in these pandemic strains, mutations were introduced in the HA gene (Bean et al., 1992). Whether similar mutations are required in the NA to enable the virus to cross host species barriers remains unknown; however, the substrate specificity of the human virus N2 NA, which was derived from an avian virus, gradually changed during its replication in humans (Baum et al., 1991). Results described hereinabove indicate that NA mutations can indeed contribute to the ability of influenza A viruses to adapt to new environments. For example, a reassortment virus with human virus NA and the remaining genes from a duck virus failed to replicate in ducks (Hinshaw et al., 1983), even though the NA of the human virus originated from an avian virus (Scholtissek et al., 1978). This suggests that mutations likely occurred in the NA gene during adaptation in humans. Comparative studies of viral NAs from different animal hosts, in conjunction with recently developed plasmid-based reverse genetics (Fodor et al., 1999; Neumann et al., 1999), may yield useful insights into how these surface glycoproteins contribute to adaptive changes among influenza viruses in nature.

References

Air et al., *Struct. Func. Genet.*, 6, 341 (1989).

Avery's Drug Treatment: Principles and Practice of Clinical Pharmacology and Therapeutics, 3$^{rd}$ edition, ADIS Press, LTD., Williams and Wilkins, Baltimore, Md. (1987).

Baum et al., *Virology*, 180, 10 (1991).

Bean et al., *J. Virol.*, 66, 1129 (1992).

Berkow et al., The Merck Manual, 15$^{th}$ edition, Merck and Co., Rahway, N.J. (1987).

Carroll et al., *Virus Res.*, 3, 165 (1985).

Ebadi, *Pharmacology*, Little, Brown and Co., Boston, Mass. (1985).

Edwards, *J. Infect. Dis.*, 169, 68 (1994).

Ewami et al., *Proc. Natl. Acad. Sci. USA*, 87, 3802 (1990).

Fodor et al., *J. Virol.*, 23, 9679 (1999).

Goodman et al., eds., Goodman and Gilman's The Pharmacological Basis of Therapeutics, 8$^{th}$ edition, Pergamon Press, Inc., Elmsford, N.Y. (1990).

Hara et al., *Anal. Biochem.*, 164, 138 (1987).

Hinshaw et al., *Virology*, 128, 260 (1983).

Hughes et al., *J. Virol.*, 74, 5206 (2000).

Ito et al., *J. Virol.*, 71, 3357 (1997).

Kawaoka et al., *J. Virol.*, 63, 4603 (1989).

Katzung, ed., Basic and Clinical Pharmacology, Fifth Edition, Appleton and Lange, Norwalk, Conn. (1992).

Kendal et al., *Infect. Immun.*, 29, 966 (1980).

Kerr et al., *Lancet*, 1, 291 (1975).

Kilbourne, *Bull. M2 World Health Org.*, 41, 643 (1969).

Kobasa et al., *J. Virol.*, 71, 6706 (1997).

Krug, R. M., ed., The Influenza Viruses, Plenum Press, New York (1989).

Lamb et al., In B. N. Fields, D. M. Knipe, and P. M. Howley (ed.), Fields Virology, 3$^{rd}$ ed. Lippincott-Raven Publishers, Philadelphia, Pa., p. 1353-1395, (1996).

Laver et al., *Virology*, 51, 383 (1973).

Liu et al., *Virology*, 194, 403 (1993).

Liu et al., *J. Virol.*, 69, 1099 (1995).

Mitnaul et al., *J. Virol.*, 74, 6015 (2000).

Mizrahi, ed, Viral Vaccines, Wiley-Liss, New York (1990).

Murphy, *Infect. Dis. Clin. Pract.*, 2, 174 (1993).

Muster et al., *Proc. Natl. Acad. Sci. USA*, 88, 5177 (1991).

Neumann et al., *Proc. Natl. Acad. Sci.*, 96, 9345 (1999).

Ogra et al., *J. Infect. Dis.*, 135, 499 (1977).

Palese et al., *Virology*, 61, 397 (1974).

Ray et al., *J. Biol. Chem.*, 268, 18 (1991).

Robertson et al., *Biologicals*, 20, 213 (1992).

Robertson et al., *Giornale di Igiene e Medicina Preventiva*, 29, 4 (1988).

Rogers et al., *Virology*, 127, 361 (1983a).

Rogers et al., *Virology*, 131, 394 (1983b).

Scholtissek et al., *Virology*, 87, 13 (1978).

Shibata et al., *J. Virol.*, 67, 3264 (1993).

Shibuya et al., *J. Biol. Chem.*, 262, 1596 (1987).

Subbarao et al., *J. Virol.*, 67, 7223 (1993).

Suzuki et al., *FEBS Lett.*, 404, 192 (1997).

Wang et al., *J. Biol. Chem.*, 263, 4576 (1988).

Webster et al., *Microbiol. Rev.*, 56, 152 (1992).

Wiley et al., *Annu. Ref. Biochem.*, 56, 3665 (1987).

Yang et al., *Virology*, 229, 155 (1997).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of preparing progeny influenza viruses, comprising:
contacting an isolated endogenously altered mutant mammalian cell or an isolated endogenously altered mutant avian cell with an amount of an influenza virus so as to yield progeny influenza viruses, wherein the endogenous alteration in the mutant cell results in decreased levels of N-acetylneuraminic acid and/or decreased levels of N-glycolylneuraminic acid relative to a corresponding wild-type mammalian cell or a corresponding wild-type avian cell.

2. The method of claim 1, wherein the mammalian cell is a swine, bovine, simian or canine cell.

3. The method of claim 1, wherein the wild-type mammalian cell is a Madin-Darby canine kidney (MDCK) cell.

4. The method of claim 1, wherein the mammalian cell is a mink cell.

5. The method of claim 1, wherein the mutant mammalian cell or the mutant avian cell has decreased levels of N-acetylneuraminic acid relative to the corresponding wild-type mammalian cell or the corresponding wild-type avian cell.

6. The method of claim 1, wherein the mutant mammalian cell or the mutant avian cell has decreased levels of N-glycolylneuraminic acid relative to the corresponding wild-type mammalian cell or the corresponding wild-type avian cell.

7. The method of claim 1, wherein the mutant mammalian cell or the mutant avian cell has decreased levels of N-acetylneuraminic acid and N-glycolylneuraminic acid relative to the corresponding wild-type mammalian cell or the corresponding wild-type avian cell.

8. The method of claim 1, wherein the mutant mammalian cell or the mutant avian cell has at least ten fold lower levels of N-acetylneuraminic acid and at least 2 fold lower levels of N-glycolylneuraminic acid relative to the corresponding wild-type mammalian cell or the corresponding wild-type avian cell.

9. The method of claim 1, wherein the mutant mammalian cell or the mutant avian cell is resistant to growth inhibition by *Maakia amurensis* lectin.

10. The method of claim 1, wherein the mutant mammalian cell or the mutant avian cell is resistant to growth inhibition by *Sambucus nigra* lectin.

11. The method of claim 1, wherein the mutant mammalian cell or the mutant avian cell is resistant to growth inhibition by a lectin that specifically binds sialic acid linked to galactose by a $\alpha(2-3)$ linkage or a $\alpha(2-6)$ linkage.

12. The method of claim 1, wherein the mutant mammalian cell or the mutant avian cell is resistant to growth inhibition by a lectin that specifically binds sialic acid linked to N-acetyl-galactosamine by a$\alpha(2-6)$ linkages.

13. The method of claim 1, wherein the progeny influenza viruses are prepared in cultures of the mutant mammalian cell or the mutant avian cell in the absence of exogenous sialidase activity.

14. The method of claim 1, wherein the influenza virus contacted with the mutant mammalian cell or the mutant avian cell is an influenza virus having a mutation in its neuraminidase gene that results in the influenza virus having reduced sialidase activity relative to a corresponding influenza virus that lacks the mutation.

15. The method of claim 14 wherein the mutation is a deletion.

* * * * *

UNITED STATES PATENT AND TRADEMARK OFFICE
CERTIFICATE OF CORRECTION

PATENT NO. : 8,679,819 B2  
APPLICATION NO. : 11/644179  
DATED : March 25, 2014  
INVENTOR(S) : Yoshihiro Kawaoka Page 1 of 1

It is certified that error appears in the above-identified patent and that said Letters Patent is hereby corrected as shown below:

In the Claims  
Column 20, line 26, in Claim 14, after "having", insert --a neuraminidase that has--, therefor Signed and Sealed this  
Twenty-seventh Day of January, 2015

Michelle K. Lee  
*Deputy Director of the United States Patent and Trademark Office*